US008318756B2

(12) United States Patent
Spector et al.

(10) Patent No.: US 8,318,756 B2
(45) Date of Patent: Nov. 27, 2012

(54) METHODS FOR ADMINISTERING DPD INHIBITORS IN COMBINATION WITH 5-FU AND 5-FU PRODRUGS

(75) Inventors: Thomas Spector, Durham, NC (US); William Paul Peters, Fernandina Beach, FL (US); Donald W. Kufe, Wellesley, MA (US); Brian Huber, Durham, NC (US)

(73) Assignee: Adherex Technologies, Inc., Ottawa (CA)

( * ) Notice: Subject to any disclaimer, the term of this patent is extended or adjusted under 35 U.S.C. 154(b) by 49 days.

(21) Appl. No.: 11/294,643

(22) Filed: Dec. 5, 2005

(65) Prior Publication Data

US 2006/0148753 A1 Jul. 6, 2006

Related U.S. Application Data

(60) Provisional application No. 60/633,034, filed on Dec. 3, 2004.

(51) Int. Cl.
*A61K 31/505* (2006.01)

(52) U.S. Cl. ............ 514/274; 514/49; 514/50; 514/256; 536/28.2; 536/28.54; 544/309; 544/313

(58) Field of Classification Search .................... 514/49, 514/50, 256, 274; 536/28.2, 28.54; 544/309, 544/313

See application file for complete search history.

(56) References Cited

U.S. PATENT DOCUMENTS

| | | | | |
|---|---|---|---|---|
| 5,476,855 | A | 12/1995 | el Kouni et al. | 514/269 |
| 5,817,664 | A * | 10/1998 | Spector et al. | 514/274 |
| 6,114,520 | A | 9/2000 | Hattori et al. | 536/28.5 |
| 6,177,436 | B1 | 1/2001 | Spector et al. | 514/274 |
| 2004/0028687 | A1 | 2/2004 | Waelti | 424/178.1 |
| 2007/0232529 | A1 * | 10/2007 | Mickle et al. | 514/11 |

FOREIGN PATENT DOCUMENTS

| | | |
|---|---|---|
| EP | 272065 B1 | 4/1993 |
| EP | 356166 B1 | 4/1994 |
| WO | WO 92/04901 | 4/1992 |
| WO | WO 95/12400 | 5/1995 |

OTHER PUBLICATIONS

Goudgaon et al., "Phenylselenenyl- and Phenylthio-substituted Pyrimidines as Inhibitors of Dihydrouracil Dehydrogenaseand Uridine Phosphorylase", 1993, Journal of Medicinal Chemistry, vol. 36, pp. 4250-4254.*

Lamont et al., "The Oral Fluoropyrimidines in Cancer Chemotherapy", Sep. 1999, Clinical Cancer Research,vol. 5, pp. 2289-2296.*

Ansfield, F. et al., "A Phase III Study Comparing the Clinical Utility of Four Regimens of 5-Fluorouracil," *Cancer* 39: 34-40, 1977.

Baker, S.D. et al., "Phase I and Pharmacologic Study of Oral Fluorouracil on a Chronic Daily Schedule in Combination With the Dihydropyrimidine Dehydrogenase Inactivator Eniluracil," *Journal of Clinical Oncology* 18(4): 915-926, Feb. 2000.

Barr, P.J. et al., "Incorporation of 5-substituted uracil derivatives into nucleic acids. Part IV. The synthesis of 5-ethynyluracil," *Nucleic Acids Research* 3(10): 2845-2849, Oct. 1976.

Barr, P.J. et al., "Synthesis of Some 5-Halogenovinyl Derivatives of Uracil and their Conversion into 2'-Deoxyribonucleosides," *Perkin Transactions* 1 (6): 1665-1670, 1981.

Bleackley, R.C. et al., "5-Cyanouracil and 5-[14C]Cyanouracil," in Nucleic Acid Chemistry. Improved and New Synthetic Procedures, Methods and Techniques, Part 2, Townsend, L.B. et al. (eds.), John Wiley & Sons, New York, 1978, pp. 927-930.

Cao, S. et al., "5-Ethynyluracil (776C85): Modulation of 5-Fluorouracil Efficacy and Therapeutic Index in Rats Bearing Advanced Colorectal Carcinoma," *Cancer Research* 54: 1507-1510, Mar. 15, 1994.

Cao, S. et al., "α-Fluoro-β-alanine: Effects on the Antitumor Activity and Toxicity of 5-Fluorouracil," *Biochemical Pharmacology* 59(8): 953-960, Apr. 15, 2000.

Chabner, B.A. et al., "Clinical Pharmacology of Cancer Chemotherapy," in Cancer Principles & Practice of Oncology, 2nd edition, 1985, pp. 287-328.

Christophidis, N. et al., "Fluorouracil Therapy in Patients With Carcinoma of the Large Bowel: A Pharmacokinetic Comparison of Various Rates and Routes of Administration," *Clinical Pharmacokinetics* 3(4): 330-336, Jul./Aug. 1978.

Cohen, J.L. et al., "Clinical Pharmacology of Oral and Intravenous 5-Fluorouracil (NSC-19893)," *Cancer Chemotherapy Reports. Part 1*, 58(5): 723-731, Sep./Oct. 1974.

Daher, G.C. et al., "Metabolism of Pyrimidine Analogues and Their Nucleosides," *Pharmacology & Therapeutics* 48(2): 189-222, 1990.

Etienne, M.C. et al., "Response to Fluorouracil Therapy in Cancer Patients: The Role of Tumoral Dihydropyrimidine Dehydrogenase Activity," *Journal of Clinical Oncology* 13(7): 1663-1670, Jul. 1995.

Finch, R.E. et al., "Plasma Levels of 5-Fluorouracil After Oral and Intravenous Administration in Cancer Patients," *British Journal of Clinical Pharmacology* 7(6): 613-617, Jun. 1979.

Fischel, J.L. et al., "Dihydropyrimidine Dehydrogenase: A Tumoral Target for Fluorouracil Modulation," *Clinical Cancer Research 1*: 991-996, Sep. 1995.

Fischel, J.-L. et al., "Dual Modulation of 5-fluorouracil Cytotoxicity Using Folinic Acid with a Dihydropyrimidine Dehydrogenase Inhibitor," *Biochemical Pharmacology* 53(11):1703-1709, Jun. 1, 1997.

Fleming, R.A. et al., "Correlation between Dihydropyrimidine Dehydrogenase Activity in PeripheralMononuclear Cells and Systemic Clearance of Fluorouracil in Cancer Patients," *Cancer Research* 52: 2899-2902, May 15, 1992.

(Continued)

*Primary Examiner* — Ali Soroush
(74) *Attorney, Agent, or Firm* — Klauber & Jackson LLC

(57) ABSTRACT

Methods for improved administration and dosing of DPD inhibitors in combination with 5-FU and/or 5-FU prodrugs are provided, comprising first administering to a patient in need thereof a DPD inhibitor that substantially eliminates activity of the enzyme and thereafter administering 5-FU or a 5-FU prodrug, wherein the level of 5-FU or 5-FU prodrug is in substantial excess of DPD inhibitor in the patient.

38 Claims, 3 Drawing Sheets

OTHER PUBLICATIONS

Grem, J.L. et al., "Inter- and intraindividual variation in dihydropyrimidine dehydrogenase activity in peripheral blood mononuclear cells," *Cancer Chemotherapy and Pharmacology* 40: 117-125, 1997.
Grem, J.L. et al., "Overview of Current Status and Future Direction of Clinical Trials With 5-Fluorouracil in Combination With Folinic Acid," *Cancer Treatment Reports* 71(12): 1249-1264, Dec. 1987.
Guo, X.-D. et al., "Pharmacokinetic and pharmacodynamic effects of oral eniluracil fluorouracil and leucovorin given on a weekly schedule," *Cancer Chemotherapy & Pharmacology* 52: 79-85, 2003.
Hein, L. et al., "Über die Darstellung von 5-Trifluormethyluracil," *Zeitschrifi für Chemie* 17(11): 415-416, Nov. 1977.
Ho, D.H. et al., "Distribution and Inhibition of Dihydrouracil Dehydrogenase Activities in Human Tissues Using 5-Fluorouracil as a Substrate," *Anticancer Research* 6(4): 781-784, Jul.-Aug. 1986.
Hohneker, J.A., "Clinical Development of Eniluracil: Current Status," *Oncology* 12(10 Suppl. 7): 52-56, Oct. 1998.
Jones, A.S. et al., "A method for the rapid preparation of 5-vinyluracil in high yield," *Nucleic Acids Research* 1(1): 105-107, Jan. 1974.
Keith, B. et al., "Impact of Two Weekly Schedules of Oral Eniluracil Given with Fluorouracil and Leucovorin on the Duration of Dihydropyrimidine Dehydrogenase Inhibition," *Clinical Cancer Research* 8: 1045-1050, May 2002.
Koenig, H. et al., "Biochemical Basis for Fluorouracil Neurotoxicity," *Archives of Neurology* 23(2): 155-160, Aug. 1970.
Kundu, N.G. et al., "Studies of Uracil Derivatives and Analogs. Synthesis of 5-(β-Trimethylsilyl)ethynyluracil and 5-Ethynyluracil," *Journal of Heterocyclic Chemistry* 19(3): 463-464, May-Jun. 1982.
Lemaire, L. et al., "Cardiotoxicity of commercial 5-fluorouracil vials stems from the alkaline hydrolysis of the drug," *British Journal of Cancer* 66(1): 119-127, Jul. 1992.
Lemaire, L. et al., "Fluoroacetaldehyde as cardiotoxic impurity in fluorouracil (Roche)," *The Lancet* 337(8740): 560, Mar. 2, 1991.
Levin, J. et al., "Clinical development of eniluracil/fluorouracil: an oral treatment for patients with solid tumors," *Investigational New Drugs* 18(4): 383-390, Nov. 2000.
Morrison, G.B. et al., "Dihydropyrimidine Dehydrogenase Deficiency: A Pharmacogenetic Defect Causing Severe Adverse Reactions to 5-Fluorouracil-Based Chemotherapy," *Oncology Nursing Forum* 24(1): 83-88, Jan./Feb. 1997.
Myers, C.E., "The Pharmacology of the Fluoropyrimidines," *Pharmacological Reviews* 33(1): Mar. 1-15, 1981.
Naguib, F.N.M. et al., "Enzymes of Uracil Catabolism in Normal and Neoplastic Human Tissues," *Cancer Research* 45: 5405-5412, Nov. 1985.
Ochoa, L. et al., "Pharmacokinetics and bioequivalence of a combined oral formulation of eniluracil, an inactivator of dihydropyrimidine dehydrogenase, and 5-fluorouracil in patients with advanced solid malignancies," *Annals of Oncology* 11: 1313-1322, 2000.
Okeda, R. et al., "Experimental neurotoxicity of 5-fluorouracil and its derivatives is due to poisoning by the monofluorinated organic metabolites, monofluoroacetic acid and α-fluoro-β-alanine," *Acta Neuropathologica* 81(1): 66-73, Nov. 1990.
Paff, M.T. et al., "Preclinical development of eniluracil: Enhancing the therapeutic index and dosing convenience of 5-fluorouracil," Investigational New Drugs 18(4): 365-371, Nov. 2000.
Petit, E. et al., "Circadian Rhythm-varying Plasma Concentration of 5-Fluorouracil during a Five-Day Continuous Venous Infusion at a Constant Rate in Cancer Patients," *Cancer Research* 48: 1676-1679, Mar. 15, 1988.
Porter, D.J.T. et al., "5-Ethynyl-2(1H)-Pyrimidinone: Aldehyde Oxidase-Activation to 5-Ethynyluracil, A Mechanism-Based Inactivator of Dihydropyrimidine Dehydrogenase," *Biochemical Pharmacology* 47(7): 1165-1171, 1994.
Schilsky, R.L. et al., "Phase I Clinical and Pharmacologic Study of Eniluracil Plus Fluorouracil in Patients With Advanced Cancer," *Journal of Clinical Oncology* 16(4): 1450-1457, Apr. 1998.
Schilsky, R.L. et al., "Randomized, Open-Label, Phase III Study of a 28-Day Oral Regimen of Eniluracil Plus Fluorouracil Versus Intravenous Fluorouracil Plus Leucovorin as First-Line Therapy in Patients With Metastatic/Advanced Colorectal Cancer," *Journal of Clinical Oncology* 20(6): 1519-1526, Mar. 15, 2002.
Spector, T. et al., "5-Ethynyluracil (776C85): Inactivation of Dihydropyrimidine Dehydrogenase in Vivo," *Biochemical Pharmacology* 46(12): 2243-2248, Dec. 14, 1993.
Spector, T. et al., "Attenuation of the Antitumor Activity of 5-Fluorouracil by (R)-5-Fluoro-5,6-dihydrouracil," *Cancer Research* 55: 1239-1241, Mar. 15, 1995.
Heslin et al., "Dihydropyrimidine dehydrogenase (DPD) rapidly regenerates after inactivation by eniluracil (GW776C85) in primary and metastatic colorectal cancer", Cancer Chemother Pharmacol, 2003, pp. 399-404, vol. 52.
Mani et al., "Multicenter phase II study to evaluate a 28-day regimen of oral fluorouracil plus eniluracil in the treatment of patients with previously untreated metastatic colorectal cancer", Journal of Clinical Oncology, 2000, vol. 18, No. 15, pp. 2894-2901.

* cited by examiner

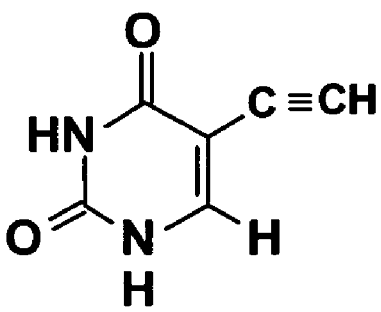
Eniluracil
(5-Ethynyluracil)
(776C85)
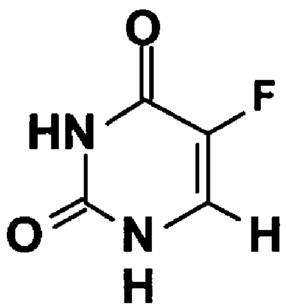
5-Fluorouracil
(5-FU)
FIGURE 1. CHEMICAL STRUCTURES OF ENILURACIL AND 5-FU.

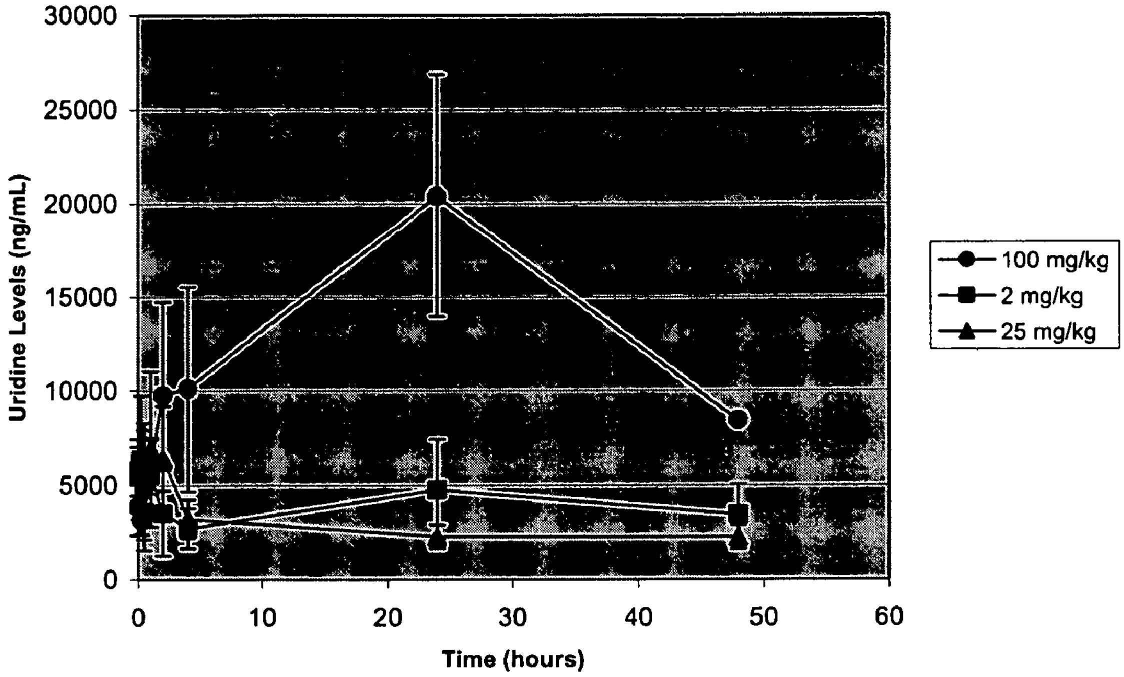
Figure 2 PLASMA URIDINE LEVELS AFTER ADMINISTRATION OF ENILURACIL

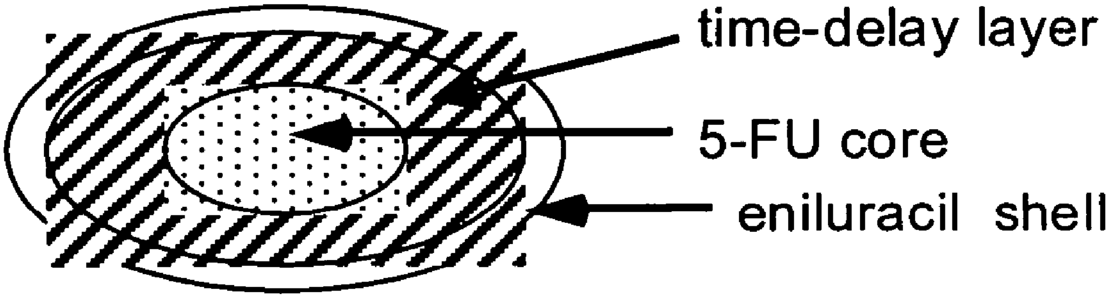
Figure 3. Combined Eniluracil and 5-FU Tablet.

METHODS FOR ADMINISTERING DPD INHIBITORS IN COMBINATION WITH 5-FU AND 5-FU PRODRUGS

BACKGROUND OF THE INVENTION

1. Field of the Invention

This invention relates generally to cancer therapy, and more particularly to cancer therapy using DPD inhibitors in combination with 5-FU and/or 5-FU prodrugs.

2. Description of the Related Art

5-Fluorouracil (5-FU) has been clinically used to treat solid tumors in cancer patients for over three decades (Ansfield et al., Cancer 39: 34-40, 1977; Grem et al., Cancer Treat Rep 71: 1249-1264, 1987; Chabner et al., Cancer, Principles and Practice of Oncology, $2^{nd}$ Ed, pp 287-328 Philadelphia, Pa.: J B Lippincott Co, 1985). 5-FU must be activated by metabolic conversion to fraudulent uridine nucleotides (e.g., FUMP, FUDP, FUTP) and deoxyuridine nucleotides (e.g., FdUMP, FdUDP, FdUTP) that interfere with DNA synthesis and RNA functions (reviewed in Meyers, Pharmacol Rev, 33: 1-15, 1981; Dasher et al., Pharmac Ther 48: 189-222, 1990). Because 5-FU differs from uracil, its natural counterpart, by only a fluorine substitution in the 5-position, it is readily activated in cancer patients. Unfortunately, its structural similarity to uracil also accounts for its rapid and extensive conversion to breakdown products that have no antitumor activity. This metabolic process is referred to as inactivation. 5-FU is rapidly inactivated by the enzyme dihydropyrimidine dehydrogenase (DPD: EC 1312, uracil reductase) (Meyers, Pharmacol Rev, 33: 1-15, 1981; Dasher et al., Pharmac Ther 48: 189-222, 1990). Therefore, the antitumor efficacy of 5-FU for treating cancer relies on the delicate balance between metabolic conversion to antitumor nucleotides (activation) and metabolic conversion to useless metabolites (inactivation).

Furthermore, several clinical issues arise due to the metabolic inactivation of 5-FU. First, because the levels of DPD vary among individuals (Fleming et al., Cancer Res 52: 2899-2902, 1992; Grem et al., Cancer Chemother Pharmacol 40: 117-125, 1997) and within individuals during the course of a day (Grem et al., Cancer Chemother Pharmacol 40: 117-125, 1997; Harris et al., Cancer Res 50: 197-201, 1990; Petit et al., Cancer Res 48: 1676-1679, 1988), the systemic levels of 5-FU produced from a given dose vary greatly and therefore render efficacy and toxicity highly unpredictable. At the extreme, patients genetically deficient in DPD experience severe and sometimes fatal toxicity when treated with 'standard' therapeutic doses of 5-FU (reviewed in Morrison et al., Oncol Nurs Forum 24: 83-88, 1997). Second, variable levels of gastrointestinal DPD (Ho et al., Anticancer Res 6: 781-784, 1986; Naguib et al., Cancer Res 45: 5405-5412, 1985; Spector et al., Biochem Pharmacol 46: 2243-2248, 1993) create highly variable absorption of orally dosed 5-FU (Christophidis et al., Clin Pharmacokinetics 3: 330-336, 1978; Cohen et al., Cancer Chemother Rep 58: 723-731, 1974; Finch et al., Br J Clin Pharmacol 7: 613-617, 1979) and therefore can result in unpredictable plasma levels of drug and produce undesirable toxicity or inadequate efficacy. Third, tumors containing high levels of DPD are less likely to respond to 5-FU-treatment (Etienne et al., J Clin Oncol 13: 1663-1670, 1995; Fischel et al., Clin Cancer Res 1: 991-996, 1995). Finally, the breakdown products of 5-FU may produce neurotoxicity (Okeda et al., Acta Neuropathol 81: 66-73, 1990; Koenig et al. Arch Neurol 23: 155-160, 1970), cardiotoxicity (et al., Lancet 337: 560, 1991; Lemaire et al., Br J Cancer 66: 119-127, 1992), palmer-plantarerythrodysaesthesia (hand-foot syndrome) (Hohneker, Oncology 12: 52-56, 1998), and GI toxicity (Spector et al., Cancer Res 55: 1239-1241, 1995) and appear to interfere with the antitumor activity (Spector et al., Cancer Res 55: 1239-1241, 1995; Cao, et al., Pharmacol 59: 953-960, 2000).

DPD is a ubiquitous enzyme that is the first and the rate-limiting step in the degradation (inactivation) of 5-FU. Studies have shown that inhibition of DPD prolongs the half-life of 5-FU in plasma. Several DPD inhibitors have been studied, including those that irreversibly inactivate DPD as well as those that reversibly inhibit DPD.

5-Ethynyluracil, also referred to as eniluracil, is an example of a DPD inhibitor that is an irreversible inactivator of DPD that reduces or eliminates the metabolic inactivation of 5-FU (for reviews see Spector et al., Drugs of The Future 19: 565-571, 1994; Paff et al., Invest. New Drugs: 18,365-371 (2000)). Due to the structural similarity between eniluracil and 5-FU, eniluracil is a substrate for DPD. As DPD attempts to break down eniluracil, the latter is converted to a highly reactive compound that irreversibly binds to DPD and thereby inactivates the enzyme. Thus, in the presence of very low amounts of eniluracil, DPD is destroyed and is no longer capable of inactivating 5-FU. Active DPD only reappears in such patients as a result of de novo DPD enzyme synthesis over a course of days.

Eniluracil has been tested in Phase I clinical trials in cancer patients (reviewed in Levin et al., Invest New Drugs 18:383-90, 2000; Baker et al., J Clin Oncol 18: 915-926 2000; Schilsky et al., J Clin Oncol 4:1450-7, 1998). It very potently eliminated DPD activity without causing toxicity. A dose of 0.74 mg/$m^2$ (about 1 mg total) eliminated greater than 90% of all DPD for prolonged periods. In fact, 24 hours after one dose of eniluracil, the level of DPD was only 3% of the predose level. The elimination half-life of 5-FU was increased from about 10 minutes to 3.5 hours by one dose of eniluracil. A dose of 3.7 mg/$m^2$ eniluracil increased the half-life of 5-FU to 4.5 hours. Higher doses added no apparent benefit.

Eniluracil has also been orally administered in Phase II and Phase III clinical trials (reviewed in Levin et al., Invest New Drugs 18:383-90, 2000; Schilsky et al., J Clin Oncol: 20:1519-26, 2002). Two dosing regimens were used in these trials. In the '5-day schedule', eniluracil was administered at a fixed dose of 50 mg per day on day-1 through day-7. 5-FU was dosed at approximately 20 mg/$m^2$ on day-2 through day-6 after the dose of eniluracil. In the '28-day schedule', eniluracil and 5-FU were co-administered in a fixed ratio of ten eniluracil to one 5-FU b.i.d. (twice daily) for 28 days. The dose of 5-FU was approximately 1 mg/$m^2$. Eniluracil abrogated the 5-FU-associated hand-foot syndrome toxicity, enabled 5-FU to be safely dosed orally, and resulted in highly predictable 5-FU plasma levels. However, the antitumor activity of these regimens was unfortunately disappointing. In two multicenter Phase III studies using the 28-day eniluracil regimen for colorectal cancer, patients receiving eniluracil and 5-FU tended to have less antitumor activity than those treated with the standard 5-FU regimen without eniluracil (Schilsky et al., J Clin Oncol: 20:1519-26, 2002).

Thus, there remains an important and unmet need in the art for identifying optimal dosing and administration schedules for DPD inhibitors used in combination with 5-FU and 5-FU prodrugs in order to maximize the antitumor efficacy and therapeutic index of 5-FU and 5-FU prodrugs, to improve the predictability of dosing and to enable 5-FU and 5-FU prodrugs to be effectively dosed by oral administration. The present invention fulfills these needs and offers other related advantages.

SUMMARY OF THE INVENTION

The present invention relates generally to improved methods for administering DPD inhibitors, such as eniluracil, in combination with 5-FU and 5-FU prodrugs. Therefore, according to one aspect of the present invention, there is provided a method for treating cancer in a patient comprising first administering a DPD inhibitor that substantially eliminates this enzyme and thereafter administering 5-FU or a 5-FU prodrug, wherein the 5-FU or 5-FU prodrug is administered at a dose such that at its time of administration the 5-FU or 5-FU prodrug is present in the patient in substantial excess of the free DPD inhibitor.

In one embodiment according to this aspect of the invention, the 5-FU or 5-FU prodrug is administered at least about 4 hours, at least about 6 hours, at least about 8 hours, at least about 10 hours, at least about 12 hours, at least about 14 hours, at least about 24 hours, or at least about 36 hours after the DPD inhibitor is administered.

In another embodiment according to this aspect of the invention, the 5-FU or 5-FU prodrug is administered about 4-72 hours, 4-36 hours, 4-24 hours, 4-14 hours, 6-14 hours or 8-14 hours after the DPD inhibitor is administered.

In another embodiment according to this aspect of the invention, the 5-FU or 5-FU prodrug is administered at a time when at least about 0.1-4 elimination half-lives, 1-4 elimination half-lives, 2-4 elimination half-lives or 3-4 elimination half-lives for the DPD inhibitor have passed since the DPD inhibitor was administered.

In another embodiment according to this aspect of the invention, the DPD inhibitor is administered at a dose sufficient to reduce DPD activity in the patient to less than about 10%, less than about 5%, less than about 3% or less than about 1% of baseline DPD activity in the patient.

In another embodiment according to this aspect of the invention, the 5-FU or 5-FU prodrug is administered at a dose such that at its time of administration the 5-FU or 5-FU prodrug is present in the patient in at least about 2-fold, at least about 3-fold, at least about 5-fold or at least about 100-fold excess of the DPD inhibitor.

In another embodiment according to this aspect of the invention, the DPD inhibitor is an irreversible DPD inhibitor.

In another embodiment according to this aspect of the invention, the DPD inhibitor is a reversible DPD inhibitor. In such embodiments, it will be understood that certain preferred reversible DPD inhibitors include tight-binding inhibitors that dissociate from DPD more slowly than excess inhibitor is eliminated from the body and therefore will not be present in substantial excess when 5-FU or the 5-FU prodrug is administered. Other preferred inhibitors include those that inhibit DPD activity but do not substantially inhibit other enzymes that activate fluorouracil, such as uridine phosphorylase (UPase), orotate phosphoribosyltransferase (OPRTase) and thymidine phosphorylase (TP).

In another embodiment according to this aspect of the invention, the 5-FU or 5-FU prodrug is selected from the group consisting of the following compounds and their 5'-esters, including phosphate esters: 5-fluorouridine, 5-fluorocytidine, 5-fluoro-2-deoxyuridine, 5-fluoro-2-deoxycytidine, and 5-fluoroarabinosyluracil.

In another embodiment according to this aspect of the invention, the 5-FU or 5-FU prodrug is selected from the group consisting of 5'-deoxy-4',5-fluorouridine, 5'-deoxy-5-fluorouridine, 1-(2-tetrahydrofuranyl)-5-fluorouracil, a 1-$C_{1-8}$ alkylcarbamoyl-5-fluorouracil derivative, 1-(2-tetrahydrofuryl)-5-fluorouracil, 5'-deoxy-5-fluoro-N-[(pentyloxy)carbonyl]-cytidine (capecitabine), or a compound that is converted to 5-FU in vivo.

In another embodiment according to this aspect of the invention, the DPD inhibitor is eniluracil or a prodrug thereof.

In another embodiment according to this aspect of the invention, the DPD inhibitor is eniluracil, and is administered at a dose of 0.8-15, 2-15, 5-15 or 2.5-5 mg/$^2$.

In another embodiment according to this aspect of the invention, the DPD inhibitor is eniluracil and the 5-FU or 5-FU prodrug is 5-FU.

In another embodiment according to this aspect of the invention, the 5-FU or 5-FU prodrug is 5-FU, and is administered at a dose 0.5-80, 0.5-40, 10-80, 10-60, 10-30 or 20-60 mg/m$^2$.

In another embodiment of the invention, the eniluracil and 5-FU or 5-FU prodrug are dosed at a ratio of about 1:3 to 1:20, 1:5 to 1:15, or 1:8 to 1:12.

In one preferred embodiment, eniluracil is first administered at a dose of about 2.5-5 mg/m$^2$ at least about 10-14 hours before administering 5-FU or 5-FU prodrug at a dose of about 15-30 mg/m$^2$ or before administering capecitabine at a dose of about 5-100 mg/m$^2$. Optionally, additional doses of 5-FU or capecitabine can be thereafter administered with or without additional dosing of eniluracil.

In another embodiment according to this aspect of the invention, the DPD inhibitor is eniluracil and the 5-FU or 5-FU prodrug is capecitabine.

In another embodiment according to this aspect of the invention, the DPD inhibitor is eniluracil, the 5-FU or 5-FU prodrug is 5-FU or capecitabine, and the eniluracil is administered at a dose between about 0.8-15, 2.5-15, 5-15 or 2.5-5 mg/m$^2$.

In another embodiment according to this aspect of the invention, the DPD inhibitor is eniluracil, the 5-FU or 5-FU prodrug is 5-FU, the eniluracil is administered at a dose between about 2.5-5 mg/m$^2$, and the 5-FU is administered at a dose between about 0.5-40 mg/m$^2$, depending on the dosing schedule used.

One illustrative schedule, e.g., a twice per day (b.i.d.) for 28 days (28-day) schedule, employs a 5-FU dose from between about 0.5-1.5 mg/m$^2$. Another illustrative schedule, e.g., a once per day for 5 days (5-day) schedule, employs a 5-FU dose from between about 10-60 mg/m$^2$. In a more particular embodiment, the 5-FU dose is between about 10-30 mg/m$^2$. In another embodiment, the 5-FU dose is between about 20-60 mg/m$^2$.

Another illustrative schedule, e.g., a once per week (weekly) schedule, can employ a 5-FU dose between about 10-80 mg/m$^2$. In a more particular embodiment, 5-FU is dosed between about 15-40 or 10-30 mg/m$^2$. In another embodiment, 5-FU is dosed between about 30-80 mg/m$^2$.

In another embodiment according to this aspect of the invention, the DPD inhibitor is eniluracil, the 5-FU or 5-FU prodrug is capecitabine, the eniluracil is administered at a dose between about 0.8-15, between about 2-15, between about 5-15 or between about 2.5-5 mg/m$^2$, and the capecitabine is administered at a dose between about 0.8-200 mg/m$^2$. In a more particular embodiment, the capecitabine is administered at a dose between about 0.8-10 mg/m$^2$ or 1.3-4 mg/m$^2$ (e.g., for certain illustrative protracted b.i.d. daily schedules).

In another embodiment according to this aspect of the invention, the DPD inhibitor comprises a 5-substituted uracil analog or a prodrug thereof.

In another embodiment according to this aspect of the invention, the DPD inhibitor comprises a uracil analog substituted in the 5-position by a halogen atom, a $C_{2-4}$ alkenyl group, a $C_{2-4}$ alkenyl group substituted by halogen, a $C_{2-6}$ alkynyl group, a $C_{2-6}$ alkynyl group substituted by a halogen, a cyano group or a $C_{1-4}$ alkyl group substituted by halogen.

In another embodiment according to this aspect of the invention, the DPD inhibitor comprises a uracil analog selected from the group consisting of eniluracil, 5-propynyluracil, 5-cyanouracil, 5-propynyluracil, 5-bromoethynyluracil, 5-(1-chlorovinyl)uracil, 5-iodouracil, 5-bromovinyluracil, (E)-5-(2-bromovinyl)uracil 5-hex-1-ynyluracil, 5-vinyluracil, 5-trifluorouracil, 5-bromouracil, and 5-(2-bromo-1-chlorovinyl)uracil.

In another embodiment according to this aspect of the invention, the DPD inhibitor is selected from the group consisting of 5-(phenylselenenyl)uracil (PSU), 5-(phenylthio)uracil (PTU), 5-(phenylselenenyl)barbituric acid and 5-(phenylthio)barbituric acid.

According to another aspect of the invention, there is provided a method for treating cancer in a patient comprising first administering eniluracil and thereafter administering 5-FU, wherein the 5-FU is administered at a dose such that at its time of administration the 5-FU is present in the patient in substantial excess of the DPD inhibitor.

In one embodiment according to this aspect of the invention, the 5-FU is administered at least about 4 hours, 6 hours, 8 hours, 10 hours, 12 hours, 14 hours, 24 hours or 36 hours after the eniluracil is administered. In one preferred embodiment, the 5-FU is administered at least about 4 hours, at least about 8 hours or at least about 12 hours after the eniluracil is administered.

In another embodiment according to this aspect of the invention, the 5-FU is administered about 4-72 hours, 4-36 hours, 4-24 hours, 4-14 hours, 6-14 hours or 8-14 hours after the eniluracil is administered. In one preferred embodiment, the 5-FU is administered about 4-14 hours after the eniluracil is administered.

In another embodiment of the invention, the 5-FU is administered at a time when between about 0.1-4 elimination half-lives, 1-4 elimination half-lives, 2-4 elimination half-lives or 3-4 elimination half-lives for the eniluracil have passed since the eniluracil was administered.

In another embodiment according to this aspect of the invention, the eniluracil is administered at a dose sufficient to reduce DPD activity in the patient to less than about 10%, less than about 5%, less than about 3% or less than about 1% of baseline DPD activity.

In another embodiment according to this aspect of the invention, the 5-FU is administered at a dose such that at its time of administration the 5-FU is present in the patient in at least about 2-fold, at least about 3-fold, at least about 5-fold or at least about 100-fold excess of the eniluracil.

In another embodiment according to this aspect of the invention, the eniluracil is administered at a dose between about 0.7-15 $mg/m^2$. In another embodiment of the invention, the eniluracil is administered at a dose between about 2.5-5 $mg/m^2$. In another embodiment of the invention, the eniluracil is administered at a dose between about 5-15 $mg/m^2$.

In another embodiment according to this aspect of the invention, the eniluracil is administered at a dose between about 2.5-5 $mg/m^2$ and the 5-FU is administered at a dose between about 0.5-40 $mg/m^2$.

According to another aspect of the present invention, there is provided a method for treating cancer in a patient comprising first administering eniluracil and thereafter administering 5-FU, wherein the eniluracil is administered at a dose between about 2.5-5 $mg/m^2$, and wherein the 5-FU is administered when between about 1-4, 2-4 or 3-4 elimination half-lives for eniluracil have passed since the eniluracil was administered.

In one embodiment according to this aspect of the invention, the 5-FU is administered at least about 4 hours, 6 hours, 8 hours, 10 hours, 12 hours or 14 hours after the eniluracil is administered.

In one embodiment according to this aspect of the invention, the 5-FU is administered between about 4-36 hours, 4-24 hours, 4-14 hours, 6-14 hours or 8-14 hours after the eniluracil is administered.

In another embodiment according to this aspect of the invention, the 5-FU is administered at a dose such that at its time of administration the 5-FU is present in the patient in at least about 2-fold, at least about 3-fold, at least about 5-fold or at least about 100-fold excess of the eniluracil.

In another embodiment according to this aspect of the invention, the 5-FU is administered at a dose between about 0.5-40 $mg/m^2$.

In a more particular embodiment, eniluracil (or another DPD inhibitor) is first administered and then multiple doses of 5-FU or 5-FU prodrug are thereafter administered at desired time points, before eniluracil (or another DPD inhibitor) is optionally administered again. For example, in one preferred embodiment, eniluracil is first administered at about 2.5 to 5 $mg/m^2$ at least about 10 to 14 hours before administration of the 5-FU or 5-FU prodrug, for example on the evening prior to the first day that either 5-FU is administered at about 15 to 30 $mg/m^2$ or capecitabine at about 5-100 $mg/m^2$ and then similar multiple doses of 5-FU or capecitabine are thereafter administered. For example, in one illustrative embodiment, eniluracil is first dosed and then multiple 5-FU or capecitabine doses are administered daily for three days each week, for example, before eniluracil is optionally administered again and the cycle repeated.

According to another aspect of the present invention, there is provided a method for treating cancer in a patient comprising first administering eniluracil and thereafter administering 5-FU, wherein the eniluracil is administered at a dose between about 2.5-5 $mg/m^2$, the 5-FU is administered when between 1-4, 2-4 or 3-4 elimination half-lives for eniluracil have passed since the eniluracil was administered, and the 5-FU is administered at a dose between about 0.5-40 $mg/m^2$.

According to another aspect of the present invention, there is provided an oral pharmaceutical time-release formulation comprising a DPD inhibitor and 5-FU or a 5-FU prodrug, wherein following administration of the formulation to a patient the 5-FU or 5-FU prodrug is not substantially released until about 0.5-36, 4-36, 4-24 or 4-14 hours after the DPD inhibitor has been released.

According to another aspect of the invention, there is provided a pharmaceutical formulation comprising a DPD inhibitor and a delivery vehicle for administering the DPD inhibitor to a patient. In another embodiment, the formulation comprises a DPD inhibitor and 5-FU or a 5-FU prodrug. In another embodiment, the formulation comprises a delivery vehicle, a DPD inhibitor and 5-FU or a 5-FU prodrug. In a particular embodiment, the delivery vehicle is a microsphere. In a related embodiment, the delivery vehicle is a microsphere that allows for the preferential or selective targeting of the DPD inhibitor to cancer cells using formulation and delivery techniques known in the art.

These and other aspects of the invention will be apparent upon reference to the following detailed description and attached figures. Patent and other documents cited herein to more specifically set forth various aspects of this invention are hereby incorporated by reference in their entireties.

BRIEF DESCRIPTION OF THE DRAWINGS

FIG. 1 shows the chemical structures of eniluracil and 5-FU.

FIG. 2 shows that eniluracil causes increased plasma uridine levels following administration in mice.

FIG. 3 shows an illustrative oral time-release formulation comprising eniluracil and 5-FU in a tablet form.

DETAILED DESCRIPTION OF THE INVENTION

As noted above, the present invention relates generally to methods for treating cancer which comprise administering to a patient at least one DPD inhibitor in combination with at least one 5-FU or 5-FU prodrug, and to compositions and formulations useful in such methods. The methods described herein are thus applicable to the treatment of essentially any cancer type in which 5-FU and/or 5-FU prodrugs have activity, including, by way of illustration but not by way of limitation, breast cancer, lung cancer, colon cancer, pancreatic cancer, gastric cancer, bladder, renal cancer, head and neck cancer, esophageal cancer, hepatocellular cancer, and all malignant leukemias and lymphomas. Moreover, because the present invention improves the antitumor efficacy of 5-FU and 5-FU prodrugs, cancer types that may have shown less than desirable responsiveness to 5-FU previously may show improved responsiveness when administered according to the methods described herein.

It has been unexpectedly discovered that DPD inhibitors such as eniluracil can inhibit the metabolic activation of 5-FU and 5-FU prodrugs and thereby compromise their antitumor activity. Therefore, according to a general aspect of the present invention, by ensuring that 5-FU or 5-FU prodrug levels are in sufficient excess of DPD inhibitor levels at the time the 5-FU or 5-FU prodrug is administered to a patient, the extent to which the DPD inhibitor may interfere with the metabolic activation of the 5-FU or 5-FU prodrug is advantageously minimized, and antitumor efficacy of these agents is thereby improved. Accordingly, in certain embodiments, an irreversible DPD inhibitor such as eniluracil should be dosed at the lowest dose that effectively inactivates DPD and sufficient time should preferably lapse to clear excess inhibitor from the blood stream before dosing with 5-FU. Moreover, as DPD can be substantially eliminated from the patient prior to administration of 5-FU or a 5-FU prodrug, the dose(s) of 5-FU or 5-FU prodrug required to achieve a desired level of therapeutic activity can be significantly reduced, thereby providing economic advantages in addition to the therapeutic advantages described herein.

It will be understood on the part of the skilled artisan, in view of this disclosure, that there exist a multitude of administration and dosing schedules that can be used in the methods described herein while ensuring that the levels of 5-FU or 5-FU prodrug at its time of administration are in a therapeutically effective amount and are in sufficient excess of DPD inhibitor level in the patient to minimize or eliminate inhibition of 5-FU metabolic activation. All such administration and dosing schedules are considered within the scope of the present invention.

In one illustrative embodiment of the invention, a DPD inhibitor is first administered (i.e., pre-dosed) to a patient in need thereof in order to substantially eliminate DPD activity in the patient, followed by administration of 5-FU or a 5-FU prodrug. By "substantially eliminate", it is meant that the level of DPD activity in the patient is reduced to at least less than 20%, less than 10%, less than 5%, less than 3% or less than 1% relative to the baseline level of DPD activity in the patient prior to administration of the DPD inhibitor. A baseline level of DPD activity for a patient can be readily determined, for example in PBMCs from the patient, using known techniques (e.g., Baker et al., J Clin Oncol 18: 915-926 2000; Schilsky et al., J Clin Oncol 4:1450-7, 1998).

After first administering at least one DPD inhibitor, and thereby substantially eliminating DPD in the patient, 5-FU or a 5-FU prodrug, or a combination thereof, is then administered to the patient after sufficient time has passed to allow the DPD inhibitor to be substantially cleared from the patient by elimination. The delay in time between administration of the DPD inhibitor and the 5-FU or 5-FU prodrug can vary provided that upon administration of the 5-FU or 5-FU prodrug, it is present in the patient in substantial excess relative to the level of DPD inhibitor remaining in the patient at that time. In one illustrative embodiment, the 5-FU or 5-FU prodrug is administered at a dose such that the level of 5-FU or 5-FU prodrug is present in the patient at least in molar excess of the DPD inhibitor remaining in the patient, for example at least about 2-fold, at least about 3-fold, at least about 5-fold or at least about 100-fold excess relative to the level of DPD inhibitor remaining in the patient at the time the 5-FU or 5-FU prodrug is administered. The skilled artisan will recognize that any of a number of known and available techniques may be used for calculating and/or determining the level of excess of 5-FU or 5-FU prodrug in a patient relative to DPD inhibitor in accordance with the embodiments described herein. Such techniques may include, for example, HPLC, LC-MS, ELISA, and others. As noted above, it is believed that by ensuring that the 5-FU or 5-FU prodrug is present in sufficient excess relative to the level of DPD inhibitor in the patient at the time the 5-FU or 5-FU prodrug is administered, interference by the DPD inhibitor with the metabolic activation of the 5-FU or 5-FU prodrug is thereby minimized, and the efficacy of the 5-FU or 5-FU prodrug is thereby improved.

In another embodiment of the invention, the 5-FU or 5-FU prodrug is administered to the patient only after at least 0.1-4 elimination half-lives, 1-4 elimination half-lives, 2-4 elimination half-lives, or 3-4 elimination half-lives of the DPD inhibitor have passed since the DPD inhibitor was administered. The elimination half-lives for certain DPD inhibitors have been determined and, for those that have not, elimination half-lives can be readily determined using well known and established gas-chromatography/mass-spec and HPLC techniques (referenced in Baker et al., J Clin Oncol 18: 915-926 2000; Schilsky et al., J Clin Oncol 4:1450-7, 1998). The elimination half-life for eniluracil in humans has been reported to be about 3.5 hours (e.g., Baker et al., J Clin Oncol 18: 915-926 2000; Ochoa et al., Ann Oncol 11:1313-22, 2000), however it is possible that the half-life for eniluracil and other DPD inhibitors may be dose-dependent and this dose dependency should be considered when determining an appropriate time delay between the administration of DPD inhibitor and 5-FU or 5-FU prodrug. Accordingly, for certain embodiments of the invention that employ eniluracil as the DPD inhibitor, in order to allow the level of eniluracil to be sufficiently decreased by elimination prior to administration of the 5-FU or 5-FU prodrug, the 5-FU or 5-FU prodrug is administered at least about 0.5 hours, about 2 hours, about 4 hours, about 6 hours, about 8 hours, about 10 hours, about 12 hours, about 14 hours, about 24 hours or about 36 hours after administration of the eniluracil. In certain other embodiments, the 5-FU or 5-FU prodrug is administered about 4-72 hours, 4-36 hours, about 4-24 hours, about 4-14 hours, about 6-14 hours or about 8-14 hours after administration of the eniluracil. Of course, it will be understood that these ranges are illustrative in nature and can be varied as necessary or desired for a particular dosing schedule provided that the presence of eniluracil is minimized or absent when 5-FU is dosed.

The DPD inhibitors used in accordance with the present invention may be either reversible or irreversible inhibitors of the DPD enzyme. Illustrative examples of reversible inhibitors of the DPD enzyme include uracil, CDHP and 3-cyano-2,6-dihydroxypyridine (CNDP). Other illustrative reversible DPD inhibitors include those described in U.S. Pat. No. 5,476,855 and WO 95/012400, the contents of which are incorporated herein by reference in their entireties, for example 5-(phenylselenenyl)uracil (PSU), 5-(phenylthio) uracil (PTU), 5-(phenylselenenyl)barbituric acid and 5-(phenylthio)barbituric acid. It will be understood that certain preferred reversible DPD inhibitors include tight-binding inhibitors that dissociate from DPD more slowly than excess inhibitor is eliminated from the body and/or those which inhibit DPD activity but do not substantially inhibit other enzymes that activate fluorouracil, such as uridine phosphorylase (UPase), orotate phosphoribosyltransferase (OPRTase) and thymidine phosphorylase (TP).

In certain preferred embodiments of the invention, the DPD inhibitor is one that irreversibly inactivates the DPD enzyme. Illustrative DPD inhibitors in this regard include, but are not limited to, DPD inhibitors comprising a 5-substituted uracil compound, or a prodrug thereof, particularly a uracil compound substituted in the 5-position by a halogen atom, a $C_{2-4}$ alkenyl group (e.g. vinyl) optionally substituted by halogen (e.g. 2-bromovinyl, 1-chlorovinyl or 2-bromo-1-chlorovinyl), a $C_{2-6}$ alkynyl group optionally substituted by a halogen atom, a cyano group, or a $C_{1-4}$ alkyl group substituted by halogen (e.g. trifluoromethyl).

In a more particular embodiment of the invention, the DPD inhibitor is selected from the group consisting of eniluracil, 5-propynyluracil, 5-cyanouracil, 5-propynyluracil, 5-bromoethynyluracil, 5-(1-chlorovinyl)uracil, 5-iodouracil, 5-bromovinyluracil, (E)-5-(2-bromovinyl)uracil, 5-hex-1-ynyluracil, 5-vinyluracil, 5-trifluorouracil, 5-bromouracil, and 5-(2-bromo-1-chlorovinyl)uracil, or a prodrug thereof.

In another embodiment, the DPD inhibitor is a prodrug of 5-bromovinyluracil, one illustrative compound being represented by the compound 1-β-D-arabinofuranosyl-(E)-5-(2-bromovinyl)uracil (also referred to as BV-araU or sorivudine). Certain illustrative prodrug compounds in this regard are described, for example, in U.S. Pat. No. 4,386,076, the disclosure of which is incorporated herein by reference.

In one preferred embodiment of the invention, the DPD inhibitor is eniluracil or a prodrug of eniluracil, such as 5-ethynyl-2(1H)-pyrimidinone (eniluracil missing the 4-oxygen) (Porter, et al., Biochem. Pharmacol 47: 1165-1171, 1994), a nucleoside or deoxynucleoside derivative of eniluracil, a compound that is converted to eniluracil in vivo, and/or a derivative of a DPD inactivator that is converted to the inactivator in vivo. By way of example, such compounds can include nucleoside derivatives which contain a nucleobase corresponding to the above 5-substituted uracil compounds, for example nucleoside derivatives containing a ribose, 2'-deoxyribose, 2',3'-dideoxyribose, arabinose or other cleavable sugar portion, which may additionally contain a 2'- or 3'-substituent such as a halogen or a 5'substituent such as an ester. More particular examples of such nucleoside derivatives include 1(β-D-arabinofuranosyl)-5-prop-1-ynyluracil and 2',3'-dideoxy-5-ethynyl-3'-fluorouridine.

Numerous 5-FU prodrugs are known which may also be used in accordance with the present invention. A prodrug of 5-FU is a compound which is metabolized in vivo to 5-fluorouracil and may include, by way of illustration, 5-fluorouridine, 5-fluorocytidine, 5-fluoro-2-deoxyuridine, 5-fluoro-2-deoxycytidine, 5-fluoroarabinosyluracil, and their 5'-esters, including phosphate esters. Other illustrative compounds include 5'-deoxy-4',5-fluorouridine, 5'-deoxy-5-fluorouridine, 1-(2-tetrahydrofuranyl)-5-fluorouracil, 1-$C_{1-8}$ alkylcarbamoyl-5-fluorouracil derivative, 1-(2-tetrahydrofuryl)-5-fluorouracil, Ftorafur (Tegafur, an oral 5-FU prodrug that is widely used in Asian countries), and 5'-deoxy-5-fluoro-N-[(pentyloxy)carbonyl]-cytidine (capecitabine, marketed by Roche Laboratories Inc. as Xeloda®), or a compound that is converted to 5-FU in vivo.

In a particularly preferred embodiment of the present invention, the methods described herein employ eniluracil in combination with 5-FU. As noted above, in order to maximize the antitumor activity of 5-FU, eniluracil is administered at a dose to substantially eliminate DPD activity in the patient while also ensuring that eniluracil is not present in excess when 5-FU is dosed. Because eniluracil is a very potent irreversible inactivator of DPD, it is preferably dosed before 5-FU. Eniluracil rapidly inactivates DPD and then is preferably given time to be substantially cleared from the patient by elimination prior to administering the 5-FU. Accordingly, DPD activity will be substantially eliminated and the levels of eniluracil will be advantageously low when 5-FU is administered to the patient.

It will be understood in view of this disclosure that the methods of the present invention can also comprise administration schedules of whatever duration and dosing characteristics desired, provided the dosing schedule is properly selected so that the 5-FU or 5-FU prodrug is present in excess of the level of eniluracil remaining in the patient at the time the 5-FU or 5-FU prodrug is administered. In one illustrative embodiment employing the particular combination of eniluracil and 5-FU, a method of the present invention comprises a once per day for 5 days (5-day) schedule or a once-per-week (weekly) schedule. For 5-day or weekly schedules, the dose-range of eniluracil will typically be between about 0.8 and 10 $mg/m^2$, preferably from about 2.5 to 5 $mg/m^2$. Note that even higher doses of eniluracil may be used provided that enough time elapses to clear the excess prior to administering 5-FU.

For convenience, a simple fixed dose of eniluracil is preferred in certain embodiments. As described herein, fixed doses in the range of about 2.5-15 mg will generally be appropriate for most patients. In certain preferred embodiments, the fixed dose is in the range of about 2.5-5 mg. Illustrative fixed doses of eniluracil that will eliminate DPD for longer than 24 hours, and in some cases for longer than 3-5 days, in patients of different sizes, are shown in the following Table.

| Body Surface Area (square meters) | Dose Eniluracil (mg) | $mg/m^2$ (range) |
|---|---|---|
| 0.5 to 1.0 | 2.5 | 2.5 to 5.0 |
| >1.0 to 2.0 | 5.0 | 2.5 to 5.0 |
| >2.0 to 4.0 | 10.0 | 2.5 to 5.0 |

In one illustrative embodiment, the time delay between eniluracil administration and 5-FU administration is between about 4-72 hours, 4-36 hours, 4-24 hours or 4-14 hours (or at least about 1-4 elimination half-lives for eniluracil). For example, eniluracil may be administered the night before 5-FU or, alternatively, can be administered in the morning followed by 5-FU administration in the evening. Using an illustrative dose for 5-FU of about 20 to 30 $mg/m^2$ for these schedules (Levin et al., Invest New Drugs 18:383-90, 2000; Schilsky et al., J Clin Oncol 4:1450-7, 1998; Guo et al., Cancer Chemother Pharmacol 52:79-85, 2003), for example, 5-FU should always be in substantial excess relative to eniluracil.

In another embodiment, an extended administration schedule, e.g., a 28-day administration schedule, may be used. One illustrative 28-day b.i.d. schedule (e.g., twice daily for 28 days) involves dosing 5-FU at about 0.5-2 $mg/m^2$, preferably about 1 $mg/m^2$ (e.g., Baker et al., J Clin Oncol 18: 915-926 2000). To ensure that eniluracil is not present in excess of a low 5-FU dose, eniluracil can be administered at about 2.5 to 5 $mg/m^2$ at least about 12 hours before starting the b.i.d. schedule, for example on the evening prior to the first day that 5-FU is administered. Then single daily eniluracil doses of between about 0.5-2 $mg/m^2$, for example 1 $mg/m^2$, can be administered about 2-8 hours, preferably about 4-6 hours before the first 5-FU dose of each day, for 28 days. This strategy ensures that 5-FU levels from the first dose are in sufficient excess of eniluracil, and that the 5-FU levels from the second 5-FU dose of the day are in sufficient excess of eniluracil. During subsequent treatment days, e.g., days 2 through 28, the level of eniluracil (e.g., when dosed at 1 $mg/m^2$) in the patient's blood should have decreased by about 50% (to 0.5 $mg/m^2$) within four hours (first daily 5-FU dose) and by about 94% (to 0.06 $mg/m^2$) by the second 5-FU dose of the day. The initial 2.5 to 5 $mg/m^2$ of eniluracil and the subsequent 1 $mg/m^2$ doses should serve to effectively eliminate DPD activity in the patient for the 28 days of 5-FU dosing.

In another illustrative embodiment, eniluracil (or another DPD inhibitor) is first administered and then multiple doses of 5-FU or 5-FU prodrug are thereafter administered at desired time points, before eniluracil is optionally administered again. For example, in an illustrative embodiment, eniluracil is first dosed and then multiple 5-FU doses are administered at illustrative time points of about 12 hours, 36 hours, and even 54 hours thereafter, if desired, before eniluracil is optionally again administered and the cycle repeated.

In a particular embodiment, eniluracil and 5-FU are dosed at a ratio of about 1:5 to 1:15 or 1:8 to 1:12.

In another embodiment of the present invention, 5-FU is dosed relatively soon after eniluracil is administered, e.g., 0-0.5-1 hour, provided in accordance with the present invention that the 5-FU in molar excess relative to eniluracil when administered.

The doses and schedules of eniluracil administration described for embodiments of the present invention differ from those used in the prior Phase II and Phase III human trials (Levin et al., Invest New Drugs 18:383-90, 2000; Schilsky et al., J Clin Oncol: 20:1519-26, 2002). Those studies used higher doses of eniluracil and dosed 5-FU either simultaneously with eniluracil or only one hour after eniluracil. Although some antitumor activity was demonstrated in the Phase III trials, the overall results were less than desired and the trials were not considered successful. It is believed that by using the methods of the present invention, improved efficacy will be achieved by ensuring that excess eniluracil is not present, and thus cannot inhibit 5-FU activation, when the 5-FU or 5-FU prodrug is administered.

The present invention includes as a further feature pharmaceutical formulations comprising at least one pharmaceutically acceptable carrier or excipient and further comprising a DPD inhibitor and/or 5-FU or a 5-FU prodrug, together in a single formulation or present as separate formulations to be administered at separate time points in accordance with the present invention. In one embodiment, the eniluracil and 5-FU are present in one or more formulations at a ratio of about 1:3 to 1:20, 1:5 to 1:15, or 1:8 to 1:12. A carrier or excipient is "pharmaceutically acceptable" in the sense of being compatible with the other ingredients of the formulation and not injurious to the patient. Formulations include, for example, those adapted for oral, rectal, nasal, topical (including buccal and sublingual), vaginal and parenteral (including subcutaneous, intramuscular, intravenous and intradermal) administration. The formulations may conveniently be presented in unit dosage form and may be prepared by any methods well known in the pharmaceutical arts. Such methods include the step of bringing into association the active ingredient with the carrier that constitutes one or more accessory ingredients. In general, the formulations are prepared by uniformly and intimately bringing into association the active ingredient with liquid carriers or finely divided solid carriers or both, and then if necessary shaping the product.

Formulations according to the present invention may be prepared and/or administered using essentially any available technique. Formulations of the present invention adapted for oral administration, for example, may be presented as discrete units such as capsules, cachets or tablets each containing a predetermined amount of an active ingredient; as a powder or granules; as a solution or a suspension in an aqueous or non-aqueous liquid; or as an oil-in-water liquid emulsion or a water-in-oil liquid emulsion. An active ingredient may also be presented as a bolus, electuary or paste. Oral administration will typically be a preferred route of administration.

A tablet may be made, for example, by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethylcellulose), lubricant, inert diluent, preservative, disintegrant (e.g., sodium starch glycollate, cross-linked povidone, cross-linked sodium caroxymethylcellulose) surface-active or dispersing agent. Molded tablets may be made by molding in a suitable machine a mixture of the powdered compound moistened with an inert liquid diluent. The tablets may optionally be coated or scored and may be formulated so as to provide controlled release of the active ingredient therein using, for example, hydroxypropylmethylcellulose in varying proportions to provide the desired release profile.

Formulations for topical administration in the mouth, for example, include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier. Formulations for rectal administration, for example, may be presented as a suppository with a suitable base comprising for example cocoa butter or a salicylate. Formulation for vaginal administration, for example, may be presented as pessaries, tampons, creams, gels, pastes, foams or spray formulations containing in addition to the active ingredient such carriers as are known in the art to be appropriate.

Formulations for parenteral administration, for example, include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Typically, liquid formulations including one or more active agents are preferably buffered to a pH of 7 to 11, generally 9.5 to 10.5. Certain unit dosage formulations may include those containing a daily dose or unit, daily sub-dose, as hereinabove recited, or an appropriate fraction thereof, of an active ingredient.

Methods for making DPD inhibitors and 5-FU prodrugs described herein are known and may be carried out using conventional methodology. For example, DPD inhibitors referred to above may be prepared by the methods described in Heterocycl. Chem. 19(3) 463-4 (1982) for the preparation of 5-ethynyluracil; J. Chem. Soc. Perkin Trans. 1(16), 1665-70 (1981) for the preparation of 5-(2-bromovinyl)uracil, 5-bromoethynyluracil and 5-(2-bromo-1-chlorovinyl)uracil; Nucleic Acid Chemistry, Vol. 2, 927-30 (1978) for the preparation 5-cyano-uracil; Nucleic Acids Research, 1 (1) 105-7 (1974) for the preparation of 5-vinyluracil; Z. Chern 17(11) 415-16 (1977) for the preparation of 5-trifluoromethyluracil; Nucleic Acids Research 3 (10),2845 (1976) for the preparation of 5-(1-chlorovinyl)uracil. Certain other compounds of the invention can be prepared in accordance with processes described in European Patent Specification No. 356166 for the preparation of 3'-fluoro-2',3'-dideoxy5-alkynyluridine compounds, such as 2',3'-dideoxy-5-ethynyl-3'-fluorouridine, and European Patent Specification No. 272065 for the preparation of 5-alkynyluracil arabinosides, such as 1-(b-D-arabinofuranosyl)-5-prop-I-ynyluracil. These and other synthetic techniques are known and available for making compounds for use in the present invention.

In one embodiment, the present invention provides a combination oral formulation in which a DPD inhibitor and 5-FU or a 5-FU prodrug are dosed together in a manner that allows for the desired temporal release of the components of the formulation into the patient. Differential time-release delivery of two components can be achieved using known techniques and materials. For example, in one embodiment, an oral formulation, e.g., in the form of a tablet, may be composed of three distinct layers, as depicted illustratively in FIG. 3. The outer layer can contain eniluracil in an immediate release formulation. The middle layer can be a time-release component (e.g., time-release buffer) that delays the release of 5-FU or 5-FU prodrug to a desired extent according to the present invention, which 5-FU or 5-FU prodrug is located in the core layer in an immediate release formulation. The DPD inhibitor and 5-FU or 5-FU prodrug are formulated in the proper doses and ratios described herein. In one preferred embodiment, the DPD inhibitor is eniluracil and the 5-FU or 5-FU prodrug is 5-FU or capecitabine.

In another embodiment, an alternative formulation can comprise known delivery vehicles, such as microspheres comprising 5-FU or 5-FU prodrug. In one embodiment, for example, 5-FU or 5-FU prodrug may be encapsulated within a shell of time-release component (e.g., time-release disintegrating buffer) and an outer layer providing immediate release of a DPD inhibitor. In one preferred embodiment, the DPD inhibitor is eniluracil and the 5-FU or 5-FU prodrug is 5-FU or capecitabine. These and other examples of illustrative combination formulations can be designed and made using known techniques to allow the appropriate time-delay between the delivery of the DPD inhibitor and the 5-FU or 5-FU prodrug in a single oral preparation.

In another embodiment, DPD inhibitor may be selectively or preferentially targeted to cancer cells and tumors. The selective effect of DPD in cancer cells and tumors will enable a longer half-life of the compounds relative to their circulating half-life, which will enable a higher steady-state level of activated nucleotides and improved therapeutic index. In one embodiment, selectively targeting DPD inhibitors such as eniluracil to tumors can be accomplished using targeted microspheres, which are well known in the art. In another embodiment, targeting is achieved using a tissue specific receptor such as the asiolglycoprotein receptor to target the compound to hepatocytes and hepatoma cells. Such targeting can be accomplished, for example, by chemically or otherwise modifying the DPD inhibitor (e.g., by placing 3-6 galactose residues on eniluracil).

In another embodiment, the methods described herein further comprise the administration of leucovorin. Leucovorin, or isovorin, the active isomer of leucovorin, is commonly used in conjunction with 5-FU for treating cancer patients. It may also be added to the above-described dosing regimens for eniluracil and 5-FU. Leucovorin has been shown to improve the antitumor efficacy of eniluracil and 5-FU in tumor-bearing rats and in tissue culture (Cao et al., Cancer Res 90:1507-1510, 1993; Fischel et al., Biochem Pharmacol 53: 1703-1709, 1997) and has been administered to patients receiving eniluracil and 5-FU (Schilsky et al., J Clin Oncol 4:1450-7, 1998; Guo et al., Cancer Chemother Pharmacol 52:79-85, 2003). Leucovorin is also advantageously available in an oral formulation.

The invention can be further understood upon consideration of the following non-limiting Example.

EXAMPLES

Example 1

Excess Eniluracil Diminishes the Antitumor Activity of Eniluracil and 5-FU

Rats were implanted with Ward carcinoma tumors and were treated with one of the following regimens after their tumors grew to 3,000 mg in weight as previously described (Cao et al., Cancer Res 90:1507-1510, 1993). Rats bearing 3,000 mg of tumor mass were dosed at Day 0, Day 7, and Day 14 with the following treatments.

| | TREATMENT | | |
|---|---|---|---|
| STUDY ARM Group | Eniluracil (mg/kg) | Eniluracil at 55 minutes (mg/kg) | 5-FU at 60 minutes (mg/kg) |
| A | 0 | 0 | 0 |
| B | 1 | 0 | 5 |
| C | 1 | 25 | 5 |

Group A rats received no treatment. Group B rats were intraperitoneally (ip) dosed with 1 mg/kg eniluracil (time (t)=0) followed by intravenous (iv) 5 mg/kg 5-FU at t=60. Group C rats were dosed ip with 1 mg/kg eniluracil (t=0) followed by 25 mg/kg eniluracil ip at t=55 minutes and by 5 mg/kg 5-FU iv at t=60 minutes. Animals were dosed once per week for three weeks. Eniluracil was also dosed ip at 1 mg/kg to rats in Groups B & C on Days 2 and 3 of each weekly treatment. The treatment for Group C mimicked the clinical trials where high levels of eniluracil were present when 5-FU was dosed.

The tumors in Group A rapidly grew to 10,000 mg and the rats were sacrificed. Tumors in Group B were rapidly eliminated while those in Group C on average decreased only slightly in size. These results demonstrate that the excess eniluracil in Group C greatly diminished the antitumor activity 5-FU, likely due to interference of eniluracil with the metabolic activation of 5-FU.

Example 2

Eniluracil Inhibits the Metabolic Activation of 5-FU to Active Nucleotides

HEK 293 cells were initially treated with eniluracil (10 μM) for 1 hour. After a washout period ranging from 4-48 hours, cells were treated with [6-$^{14}$C]-5-FU (66 μM) for 2 hours at 37 degrees C. Controls were HEK 293 cells treated for 2 hours either with [6-$^{1-4}$C]-5-FU (66 μM) alone, or with eniluracil (10 μM) and [6-$^{14}$C]-5-FU (66 μM) co-administered together without preincubation. Reverse phase HPLC with radioactivity detection was utilized to quantify [6-$^{14}$C]-5-FU catabolites/anabolites present in cell lysates. In a separate set of experiments cytotoxicity of 5-FU at different eniluracil dose schedules was examined. HEK 293 cells were treated with a range of 5-FU concentrations for 72 hours at 37 degrees C. following 1 hour eniluracil (5 μM) preincubation, without eniluracil, or with eniluracil (5 μM) co-administered without preincubation. Cytotoxicity was assessed by the MTS proliferation assay and the $EC_{50}$ values for 5-FU calculated.

Pre-treatment of cells with eniluracil for 1 hour, followed by a 36 hour or a 48 hour wash out prior to [6-$^{14}$C]-5-FU treatment produced significant increases in [6-$^{14}$C]-FUMP anabolite formation compared to [6-$^{14}$C]-5-FU treatment alone, or eniluracil and [6-$^{14}$C]-5-FU co-administration ($p$-values<0.05). For example, the 48 hour washout produced a 70% increase in [6-$^{14}$C]-FUMP formation versus [6-$^{14}$C]-5-FU treatment alone, and a 41% increase in [6-$^{14}$C]-FUMP formation versus eniluracil and [6-$^{14}$C]-5-FU co-administration. In cytotoxicity experiments, pre-treatment with eniluracil for 1 hour increased the cytotoxicity of 5-FU with a decreased $EC_{50}$ value (264.0 nM±1.7) (mean±SE) compared to the 5-FU treatment alone (311.4 nM±1.1) or the EU and 5-FU co-administration without preincubation (307.8 nM±1.03) ($p<0.05$).

These results further confirm a role for eniluracil in inhibiting the anabolic pathways that convert 5-FU to active antitumor nucleotides, in addition to its known role in inhibiting the catabolic pathways that degrade 5-FU to inactive forms.

Example 3

Eniluracil Causes Plasma Uridine Levels to Increase

While eniluracil inhibition is known to cause an increase in uracil levels due to DPD inhibition, inhibitory effects on other enzymes that anabolize fluoropyrimidines would be expected to quantitatively alter the levels of other anabolites, such as uridine. Eniluracil was administered to mice at 2 mg/kg, 25 mg/kg and 100 mg/kg. Plasma samples were taken at 0 minutes, 15 minutes, 30 minutes, 60 minutes, 2 hours, 24 hours and 48 hours. Uridine levels were determined by LC-MS technology using known techniques and standards were used to validate the assay.

Results from these experiments, shown in FIG. 2, demonstrate that eniluracil causes an increase in uridine levels following administration. This finding is consistent with eniluracil having an inhibitory effect on anabolic enzymes such as uridine phosphorylase, and further supports a role for eniluracil in inhibiting the anabolic conversion of 5-FU to active nucleotides.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for treating cancer in a patient, wherein the cancer is a cancer type in which 5-FU or 5-FU prodrugs have activity, comprising first administering a DPD inhibitor, wherein the DPD inhibitor is eniluracil and the eniluracil is administered at a dose between about 2.5-5 mg/m$^2$, and 4-24 hours thereafter administering 5-FU or a 5-FU prodrug, wherein the 5-FU or 5-FU prodrug is administered at a dose such that at its time of administration the 5-FU or 5-FU prodrug is present in the patient in at least 5-fold excess of the DPD inhibitor to minimize the extent to which the DPD inhibitor can interfere with metabolic activation of the 5-FU or the 5-FU generated from the 5-FU prodrug and compromise 5-FU antitumor activity.

2. The method of claim 1, wherein the 5-FU or 5-FU prodrug is administered at least 12 hours after the DPD inhibitor is administered.

3. The method of claim 1, wherein the 5-FU or 5-FU prodrug is administered at least 14 hours after the DPD inhibitor is administered.

4. The method of claim 1, wherein the 5-FU or 5-FU prodrug is administered at a time when at least 3 elimination half-lives for the DPD inhibitor have passed since the DPD inhibitor was administered.

5. The method of claim 1, wherein the 5-FU or 5-FU prodrug is selected from the group consisting of 5-fluorouridine, 1 (2 tetrahydrofuryl)-5-fluorouracil, and 5'-deoxy-5-fluoro-N-[(pentyloxy)carbonyl]-cytidine (capecitabine).

6. The method of claim 1, wherein the 5-FU or 5-FU prodrug is 5-FU or capecitabine.

7. The method of claim 1, wherein the 5-FU or 5-FU prodrug is 5-FU, and the 5-FU is administered at a dose between about 10-60 mg/m$^2$.

8. The method of claim 1, wherein the 5-FU or 5-FU prodrug is 5-FU, and the 5-FU is administered at a dose between about 10-30 mg/m$^2$.

9. The method of claim 1, wherein the 5-FU or 5-FU prodrug is 5-FU, and the 5-FU is administered at a dose between about 20-60 mg/m$^2$.

10. A method for treating cancer in a patient, wherein the cancer is a cancer type in which 5-FU has activity, comprising first administering eniluracil and 24 hours thereafter administering 5-FU, wherein the eniluracil is administered at a dose between about 2.5-5 mg/m$^2$, and wherein the 5-FU is administered at a dose such that at its time of administration the 5-FU is present in the patient in at least 5-fold excess of the DPD inhibitor to minimize the extent to which the DPD inhibitor can interfere with metabolic activation of the 5-FU and compromise 5-FU antitumor activity.

11. The method of claim 10, wherein the 5-FU is administered at least 12 hours after the eniluracil is administered.

12. The method of claim 10, wherein the 5-FU is administered when at least 3 elimination half-lives for eniluracil have passed since the eniluracil was administered.

13. The method of claim 10, wherein the 5-FU is administered at least 14 hours after the eniluracil is administered.

14. The method of claim 10, wherein the 5 FU is administered at a dose between about 10-60 mg/m$^2$.

15. A method for treating cancer in a patient, wherein the cancer is a cancer type in which 5-FU has activity, comprising first administering eniluracil and thereafter administering 5-FU, wherein the eniluracil is administered at a dose between about 2.5-5 $mg/m^2$, and wherein the 5-FU is administered after 1-4 elimination half-lives for eniluracil have passed since the eniluracil was administered, wherein at its time of administration the 5-FU is present in the patient in at least 5-fold excess of the eniluracil to minimize the extent to which the eniluracil can interfere with metabolic activation of the 5-FU and compromise 5-FU antitumor activity.

16. The method of claim 15, wherein the 5-FU is administered at least 4 hours after the eniluracil is administered.

17. The method of claim 15, wherein the 5-FU is administered at least 14 hours after the eniluracil is administered.

18. The method of claim 15, wherein the 5-FU is administered at least 3 elimination half-lives after the eniluracil is administered and the doses of the eniluracil and the 5-FU are at a ratio of 1:5 to 1:15.

19. The method of claim 15, wherein the doses of the eniluracil and the 5-FU are at a ratio of 1:8 to 1:12.

20. The method of claim 15, wherein the 5-FU is administered at a dose between about 10-60 $mg/m^2$.

21. A method for treating cancer in a patient, wherein the cancer is a cancer type in which 5-FU has activity, comprising first administering eniluracil and thereafter administering 5-FU, wherein the eniluracil is administered at a dose between about 2.5-5 $mg/m^2$, the 5-FU is administered 4-24 hours after the eniluracil is administered, and the 5-FU is administered at a dose between about 10-60 $mg/m^2$, wherein at its time of administration the 5-FU is present in the patient in at least 5-fold excess of the eniluracil to minimize the extent to which the eniluracil can interfere with metabolic activation of the 5-FU and compromise 5-FU antitumor activity.

22. The method of claim 21, wherein the 5-FU is administered at least 14 hours after the eniluracil is administered.

23. The method of claim 21, wherein the 5-FU is administered at least 18 hours after the eniluracil is administered.

24. A method for treating cancer in a patient, wherein the cancer is a cancer type in which capecitabine has activity, comprising first administering eniluracil and thereafter administering capecitabine, wherein the eniluracil is administered at a dose between about 2.5-5 $mg/m^2$, and wherein the capecitabine is administered after 1-4 elimination half-lives for eniluracil have passed since the eniluracil was administered, wherein at its time of administration the capecitabine is present in the patient in at least 5-fold excess of eniluracil to minimize the extent to which the eniluracil can interfere with metabolic activation of 5-FU generated from the capecitabine and compromise 5-FU antitumor activity.

25. The method of claim 24, wherein the capecitabine is administered at least 4 hours after the eniluracil is administered.

26. The method of claim 24, wherein the capecitabine is administered at least 14 hours after the eniluracil is administered.

27. The method of claim 24, wherein the capecitabine is administered at least 3 elimination half-lives after the eniluracil is administered.

28. The method of claim 24, wherein the capecitabine is administered at a dose between about 0.8-200 $mg/m^2$.

29. The method of claim 24, wherein the capecitabine is administered at a dose between about 5-100 $mg/m^2$.

30. The method of claim 1, wherein the doses of the DPD inhibitor and the 5-FU or 5-FU prodrug are at a ratio of up to 1:20.

31. The method of claim 1, wherein the doses of the DPD inhibitor and the 5-FU or 5-FU prodrug are at a ratio of 1:5 to 1:15.

32. The method of claim 1, wherein the doses of the DPD inhibitor and the 5-FU or 5-FU prodrug are at a ratio of 1:8 to 1:12.

33. The method of claim 1, wherein the 5-FU or 5-FU prodrug is administered at a time when at least 4 elimination half-lives for the DPD inhibitor have passed since the DPD inhibitor was administered.

34. The method of claim 10, wherein the 5-FU or 5-FU prodrug is administered at a time when at least 4 elimination half-lives for the DPD inhibitor have passed since the DPD inhibitor was administered.

35. The method of claim 1, wherein the 5-FU prodrug is administered at a dose between about 5-100 $mg/m^2$.

36. The method of claim 1, wherein the 5-FU or 5-FU prodrug is 5-FU, and the 5-FU is administered at a dose between about 15-30 $mg/m^2$.

37. The method of claim 1, wherein the eniluracil is administered at a dose of 10 mg.

38. The method of claim 1, wherein the eniluracil is administered at a dose of 5 mg.

* * * * *

UNITED STATES PATENT AND TRADEMARK OFFICE

CERTIFICATE OF CORRECTION

PATENT NO. : 8,318,756 B2
APPLICATION NO. : 11/294643
DATED : November 27, 2012
INVENTOR(S) : Thomas Spector et al.

It is certified that error appears in the above-identified patent and that said Letters Patent is hereby corrected as shown below:

Column 16, claim 10, line 48 after “eniluracil and” delete “24” and insert -- 4-24 --.

Signed and Sealed this
Twenty-sixth Day of February, 2013

Teresa Stanek Rea
*Acting Director of the United States Patent and Trademark Office*